US011564664B2

(12) United States Patent
Kang

(10) Patent No.: US 11,564,664 B2
(45) Date of Patent: Jan. 31, 2023

(54) ULTRASOUND DIAGNOSTIC APPARATUS AND CONTROL METHOD THEREOF

(71) Applicant: Samsung Medison Co., Ltd., Gangwon-do (KR)

(72) Inventor: Seung Cheon Kang, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 70 days.

(21) Appl. No.: 17/119,505

(22) Filed: Dec. 11, 2020

(65) Prior Publication Data

US 2021/0177381 A1 Jun. 17, 2021

(30) Foreign Application Priority Data

Dec. 16, 2019 (KR) .................. 10-2019-0168218

(51) Int. Cl.
*A61B 8/00* (2006.01)
*A61B 8/14* (2006.01)
*A61B 8/08* (2006.01)

(52) U.S. Cl.
CPC .............. *A61B 8/54* (2013.01); *A61B 8/145* (2013.01); *A61B 8/4444* (2013.01); *A61B 8/4494* (2013.01); *A61B 8/5269* (2013.01)

(58) Field of Classification Search
CPC ....... A61B 8/54; A61B 8/4444; A61B 8/4494; A61B 8/5269; A61B 8/58; A61B 8/4483; G01S 7/5205
See application file for complete search history.

(56) References Cited

U.S. PATENT DOCUMENTS

| 5,517,994 A | * | 5/1996 | Burke | ................... G01S 7/5205 600/443 |
| 6,565,510 B1 | | 5/2003 | Haider | |
| 6,875,178 B2 | | 4/2005 | Phelps et al. | |

(Continued)

FOREIGN PATENT DOCUMENTS

| JP | H05-063508 U | 8/1993 |
| JP | H0563508 U | 8/1993 |

(Continued)

OTHER PUBLICATIONS

Extended European Search Report dated May 6, 2021 issued in European Patent Application No. 20213293.2.

*Primary Examiner* — Bill Thomson
*Assistant Examiner* — Tommy T Ly
(74) *Attorney, Agent, or Firm* — Morgan, Lewis & Bockius LLP

(57) ABSTRACT

An ultrasound diagnostic apparatus in accordance with one aspect of the disclosure includes: a plurality of channels configured to transmit and receive signal with a plurality of transducer elements comprised in a probe; a beamformer configured to perform beamforming a signal received from a preset number of active channel among the plurality of channels; a switch configured to connect the probe and the plurality of channels; and a controller configured to determine a faulty channel among the plurality of channels, compare whether the number of the plurality of channels is greater than or equal to the number of the plurality of transducer elements and control the switch based on the comparison result when the faulty channel is comprised in the active channel.

11 Claims, 11 Drawing Sheets

(56) References Cited

U.S. PATENT DOCUMENTS

| | | | |
|---|---|---|---|
| 2003/0028341 A1* | 2/2003 | Fallon | G01S 7/52034 |
| | | | 702/117 |
| 2014/0088431 A1 | 3/2014 | Miyazawa | |
| 2015/0071030 A1 | 3/2015 | Hayashi | |
| 2020/0088862 A1* | 3/2020 | Lundberg | G06N 3/08 |

FOREIGN PATENT DOCUMENTS

| | | | |
|---|---|---|---|
| JP | 2003-210458 A | | 7/2003 |
| JP | 2003210458 A | * | 7/2003 |
| JP | 2012-050468 A | | 3/2012 |

* cited by examiner

[FIG 1]
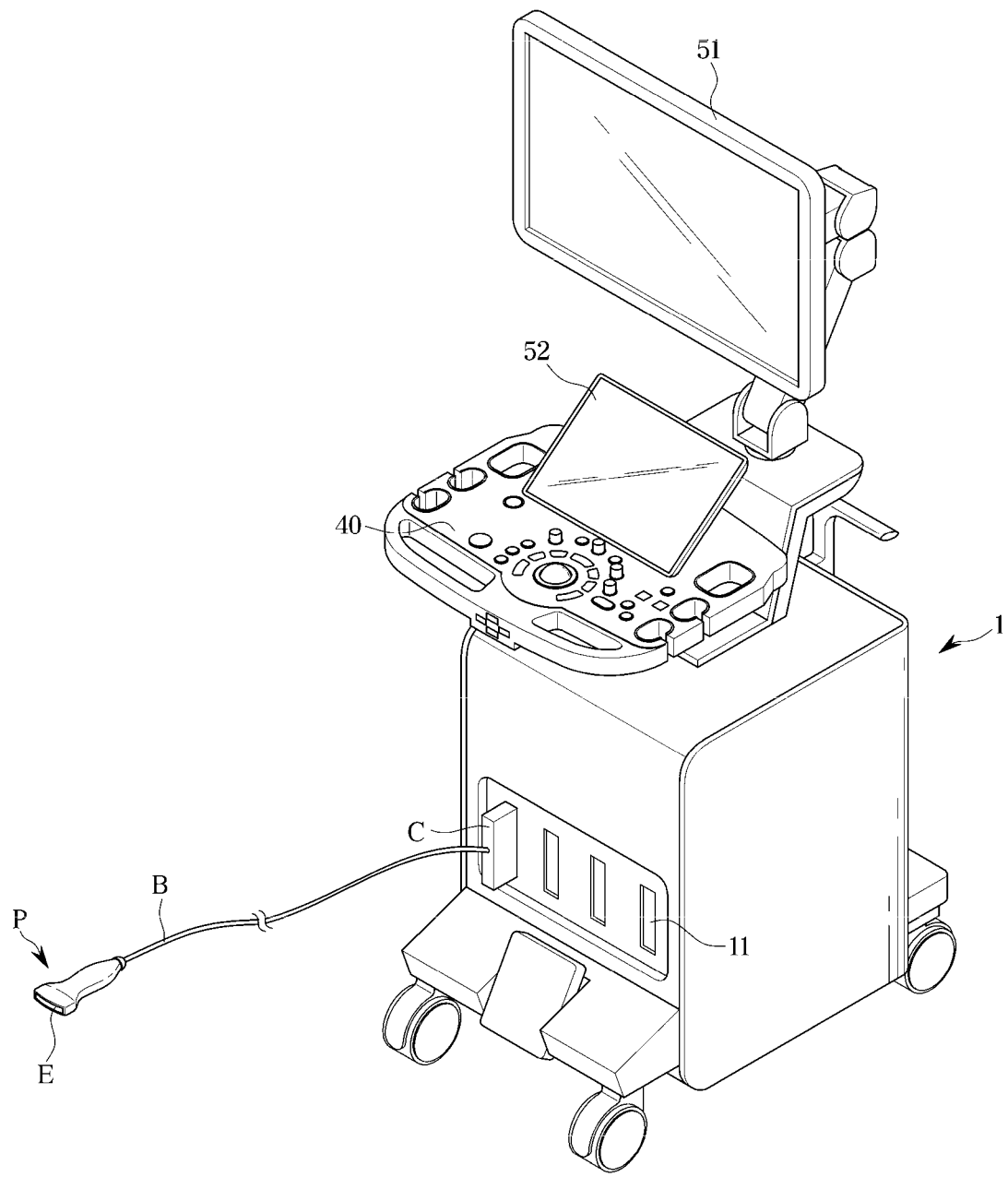

[FIG 2]
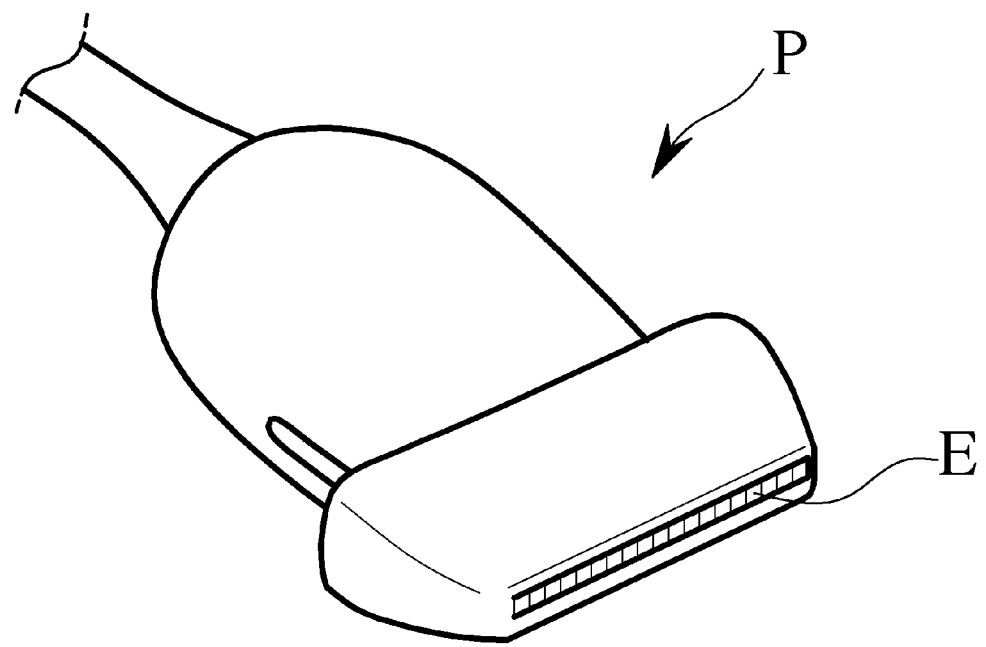

[FIG 3]
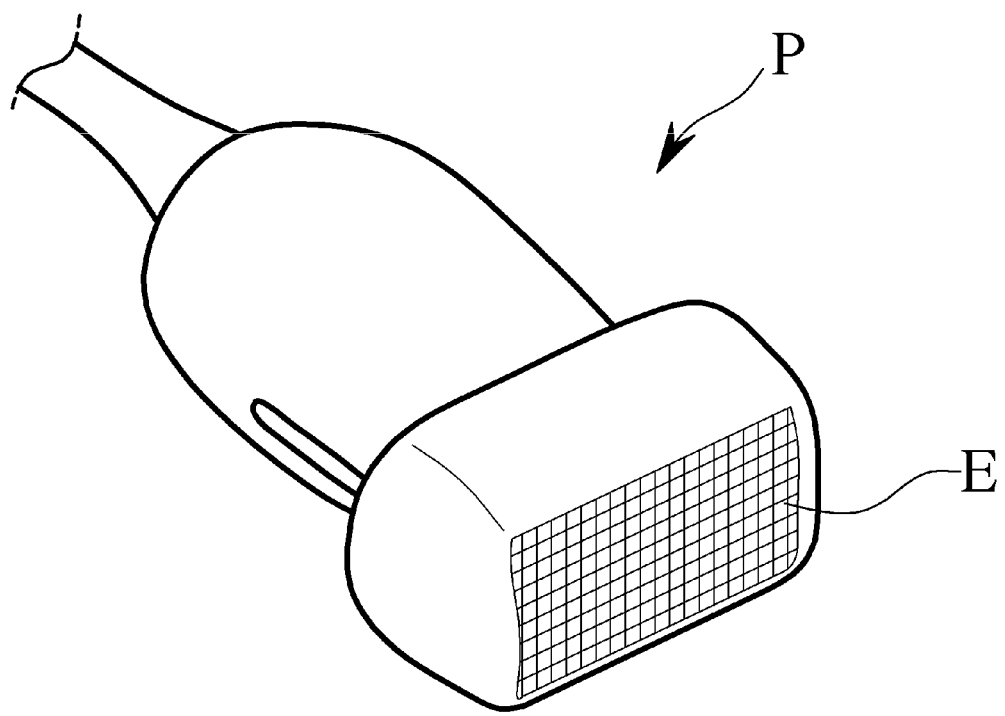

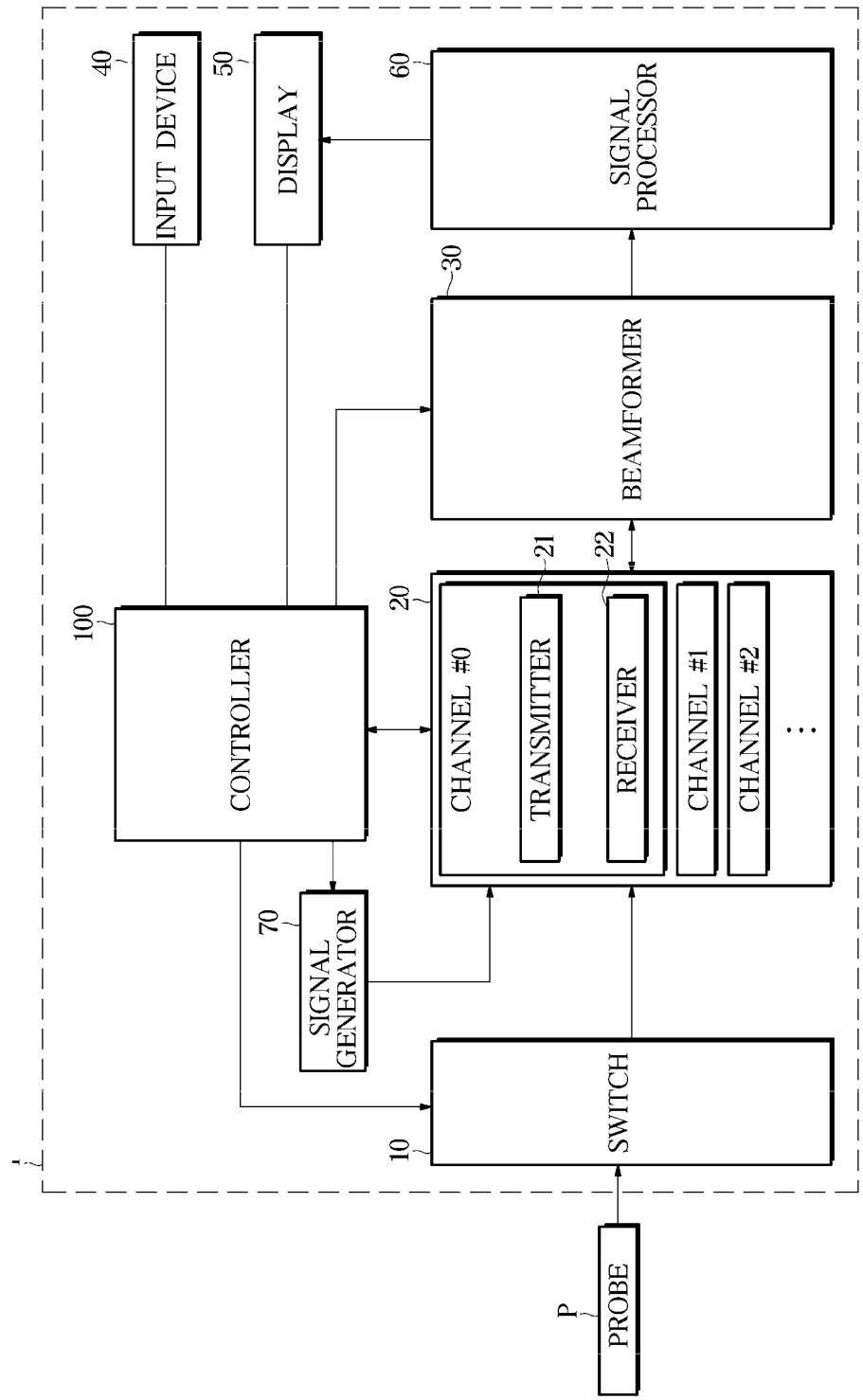

[FIG 5]
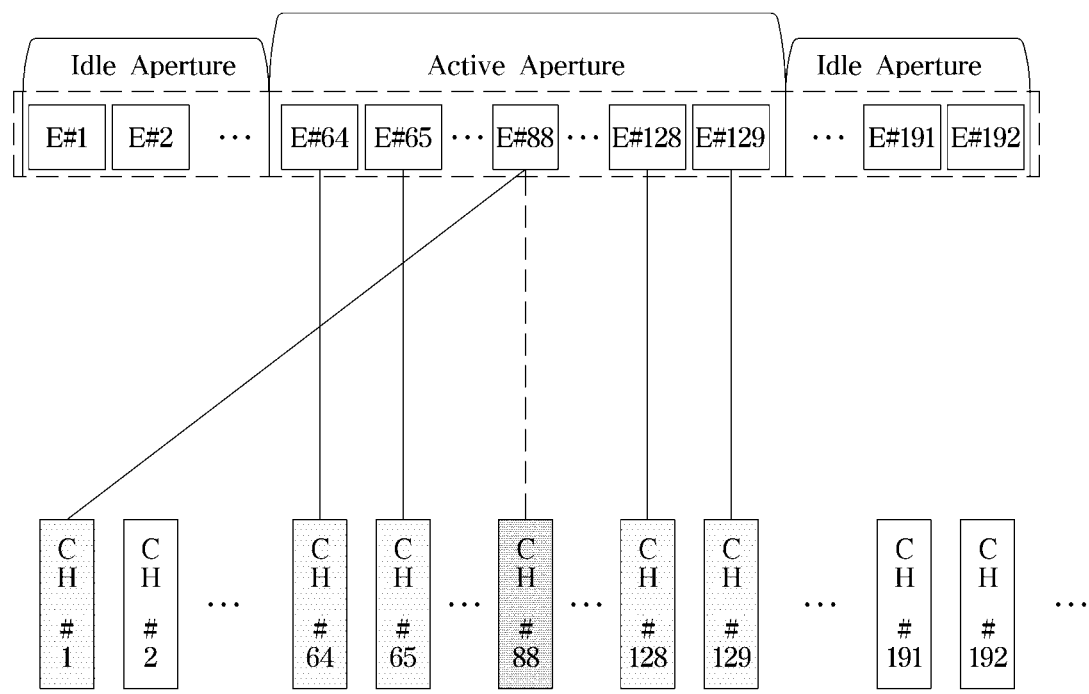

[FIG 6]
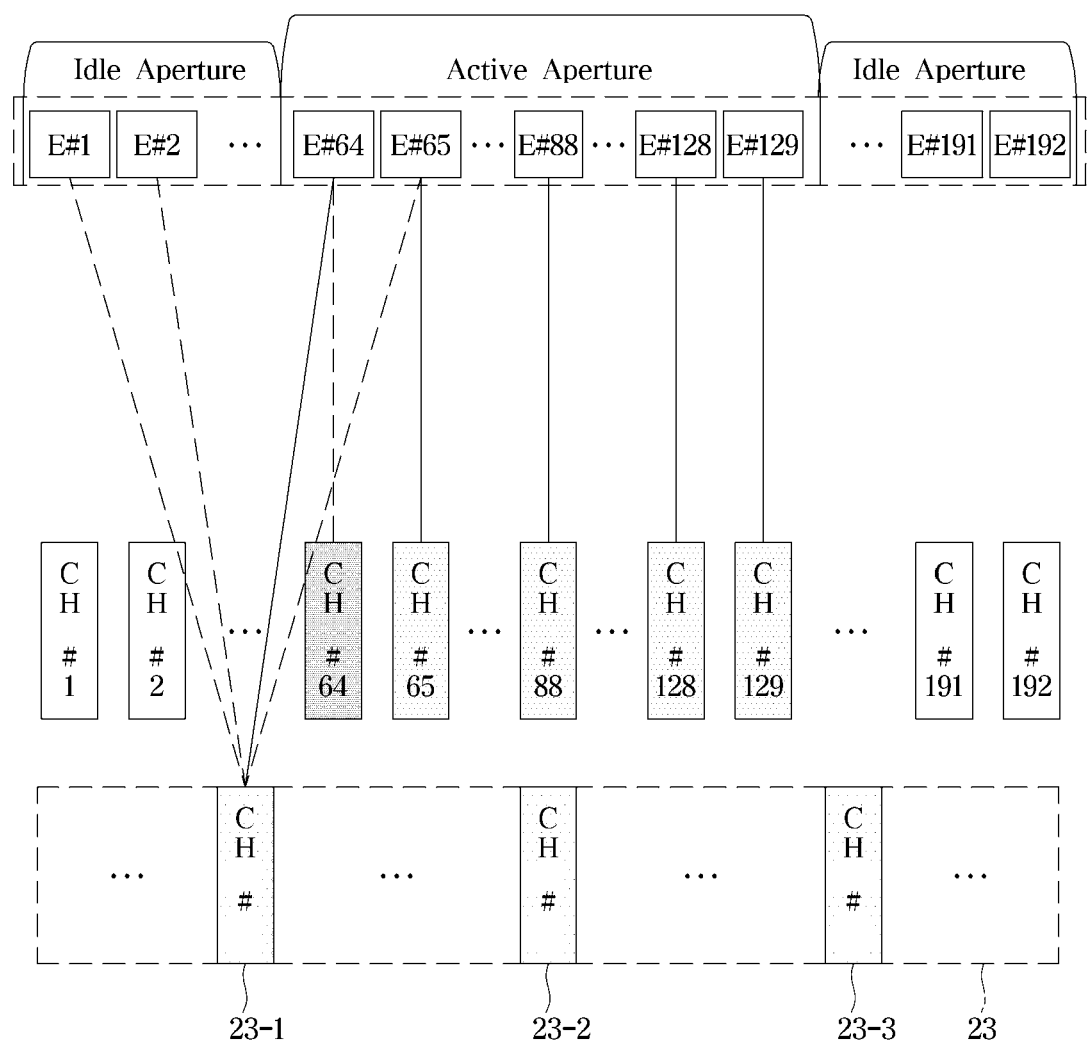

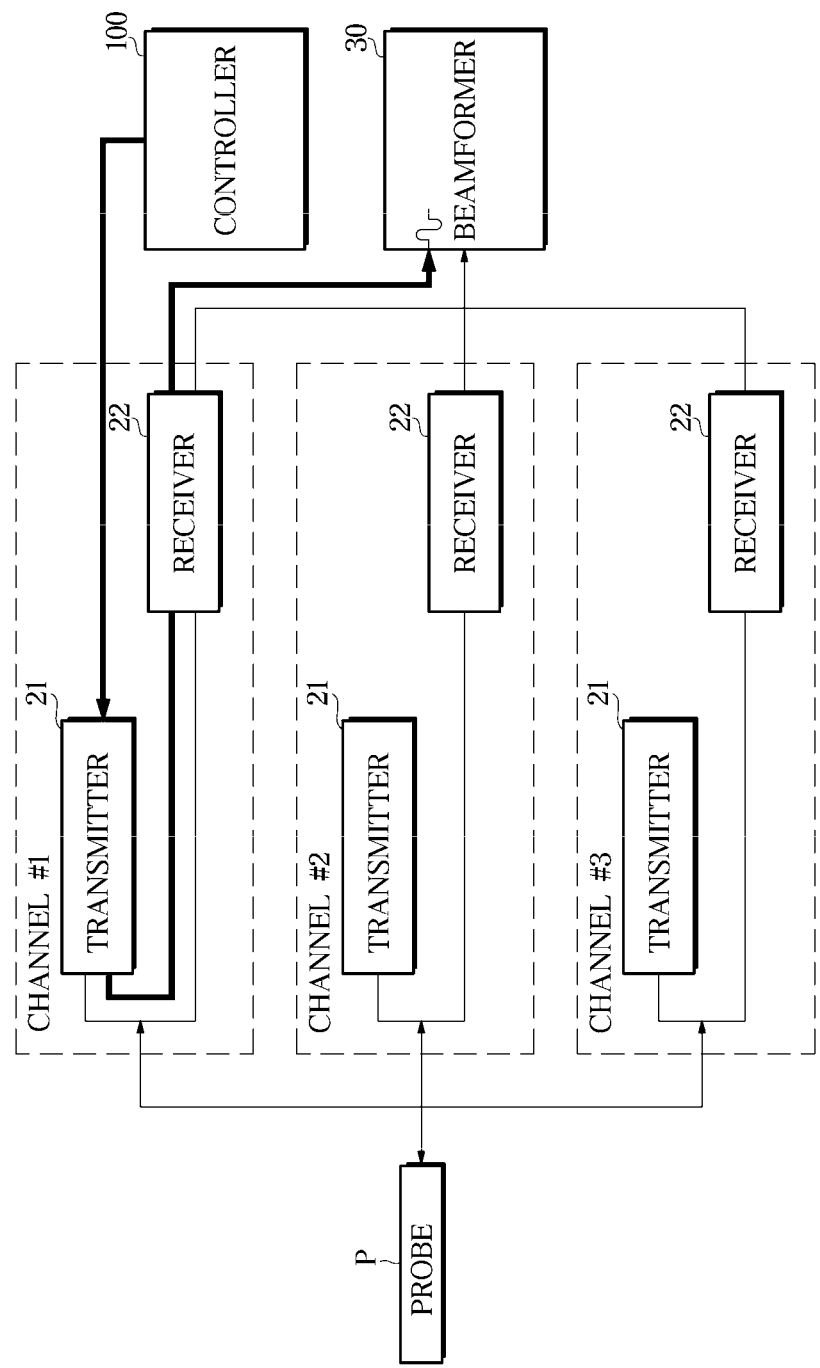

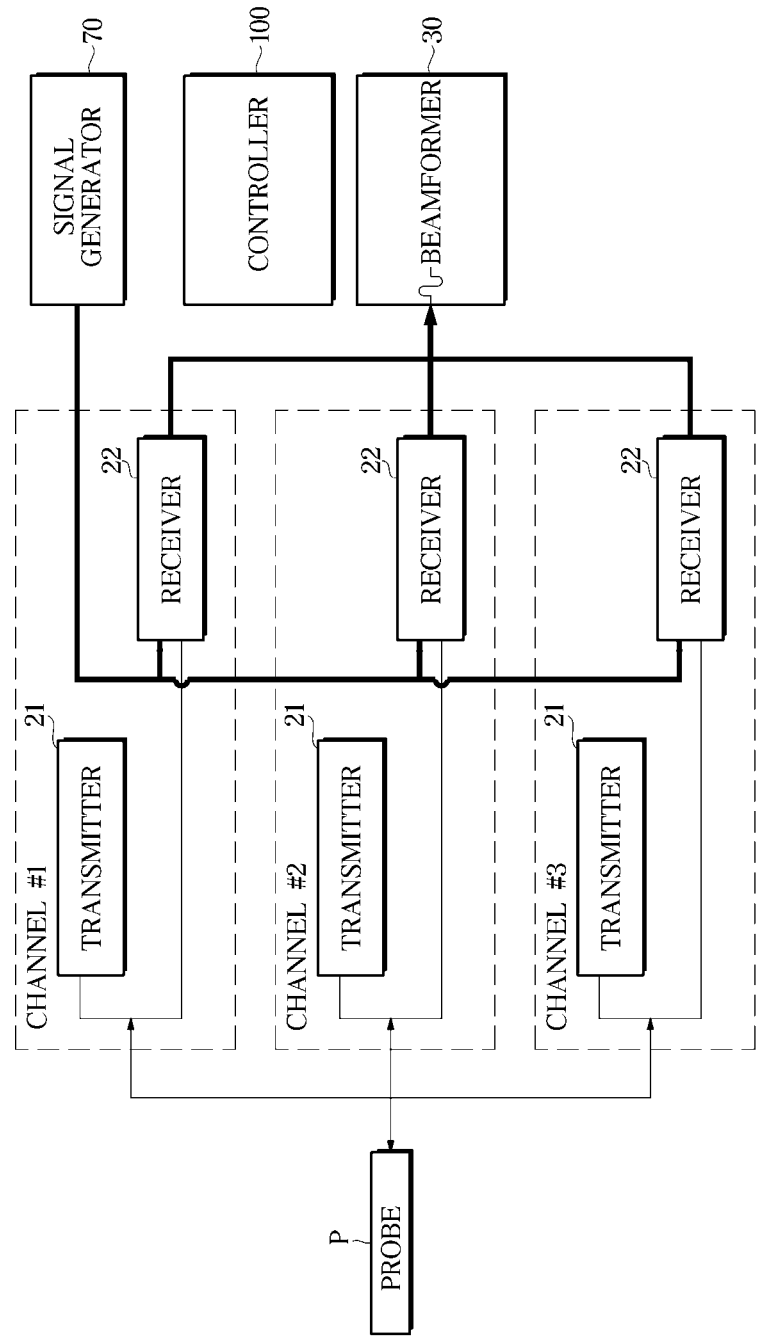

[FIG 9]
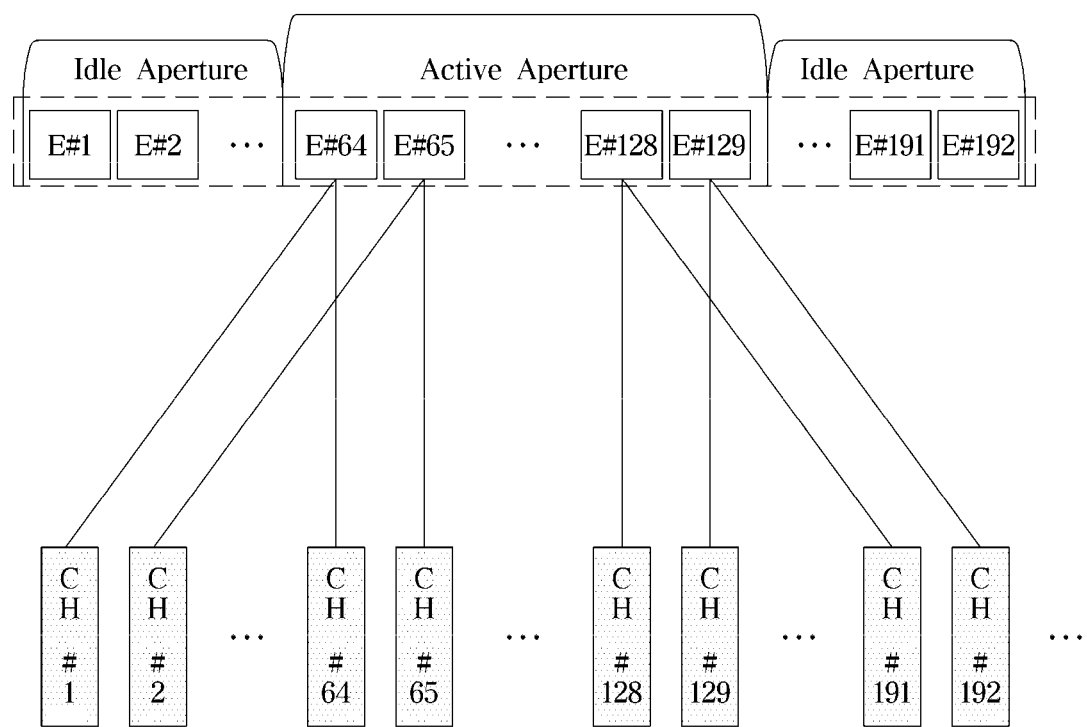

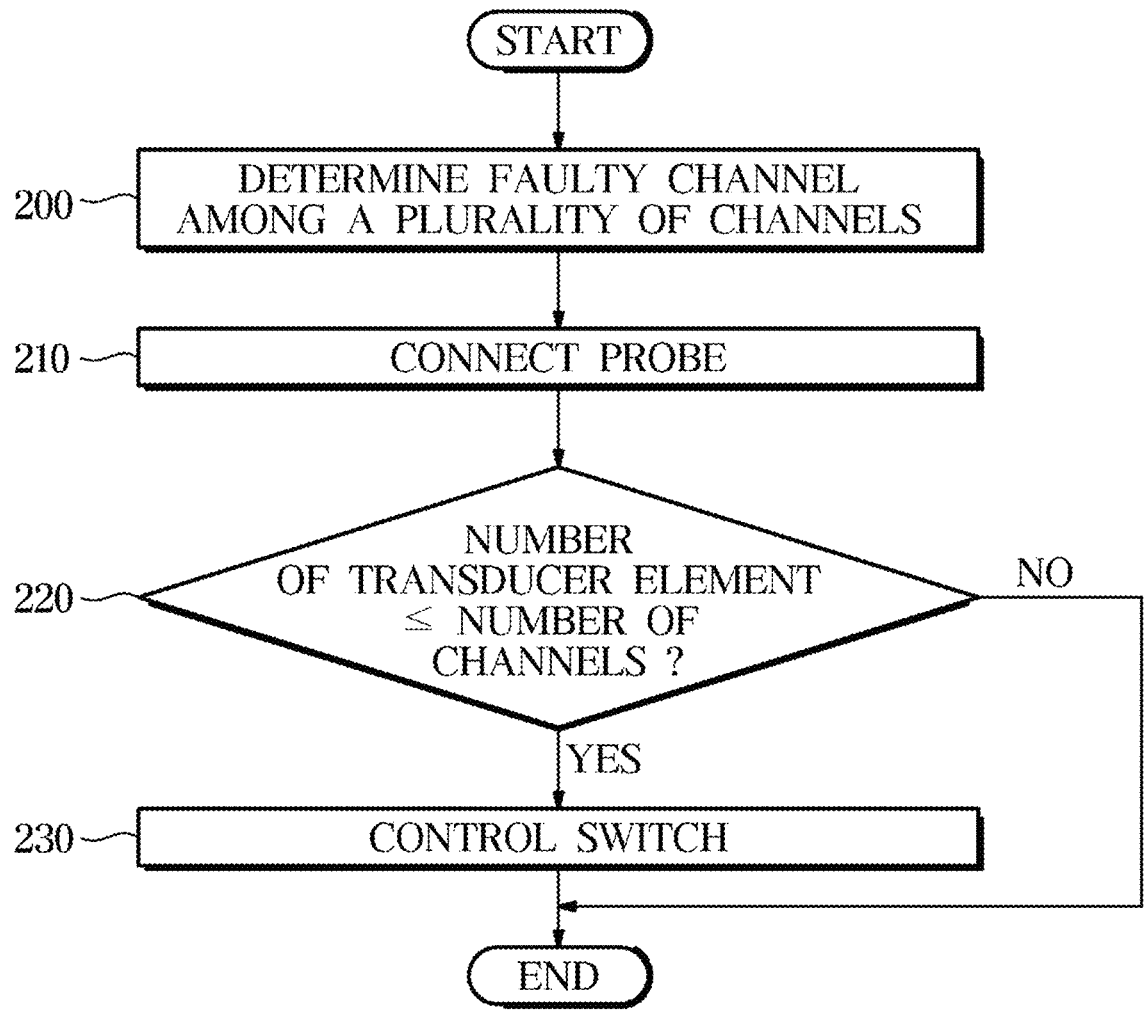

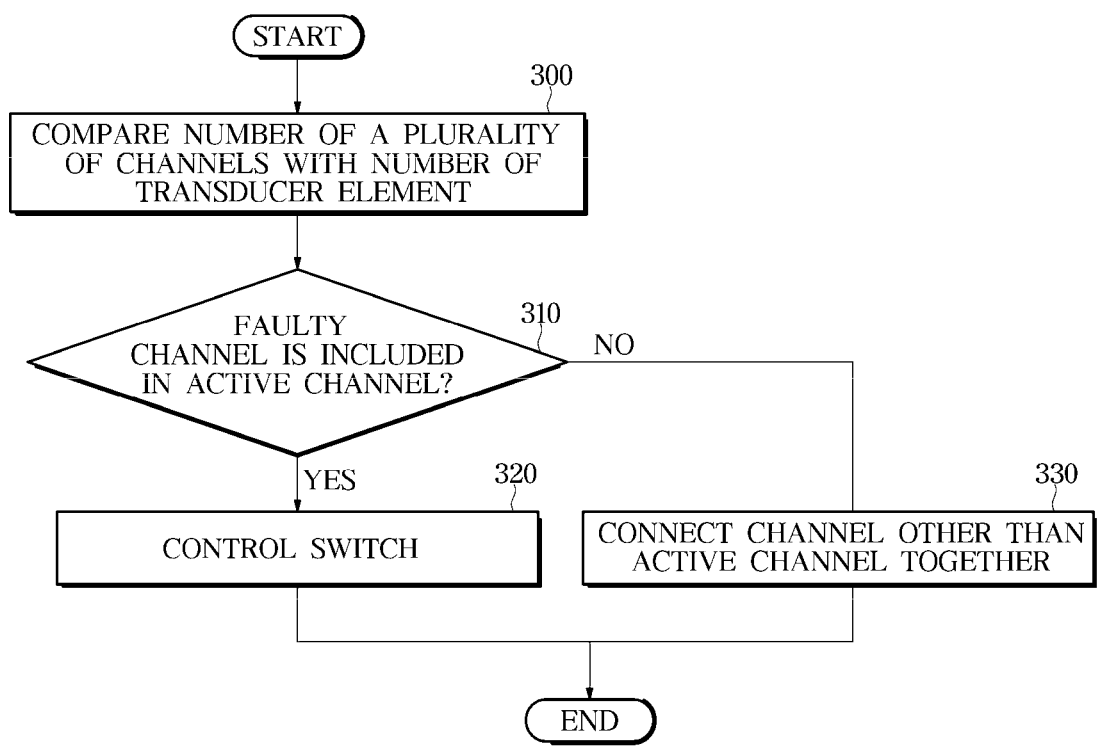
[FIG 11]

ULTRASOUND DIAGNOSTIC APPARATUS AND CONTROL METHOD THEREOF

CROSS-REFERENCE TO RELATED APPLICATION

This application is based on and claims priority under 35 U.S.C. § 119 to Korean Patent Application No. 2019-0038284, filed on Apr. 2, 2019 and Korean Patent Application No. 2019-0168218, filed on Dec. 16, 2019 in the Korean Intellectual Property Office, the disclosure of which is incorporated herein by reference.

BACKGROUND

1. Technical Field

The disclosure relates to an ultrasound diagnostic apparatus receiving an ultrasound image from a probe and a control method of the ultrasound diagnostic apparatus.

2. Description of the Related Art

An ultrasound diagnostic apparatus irradiates an ultrasound signal generated from a transducer of a probe to an object, receives information of a signal reflected from the object, and obtains at least one image of a part (eg, soft tissue or blood flow) inside the object.

The ultrasound diagnostic apparatus is compact, inexpensive, non-invasive and non-destructive when compared to other imaging devices such as X-ray devices, CT scanners, MRI, nuclear medicine diagnostic devices, etc. and is widely used for diagnosis of gynecology, heart, abdomen and urology.

A probe including a transducer for irradiating an ultrasound signal to an object and receiving an ultrasound echo signal reflected from the object may be connected to the ultrasound diagnostic apparatus. The ultrasound diagnostic apparatus includes a transceiver (hereinafter referred to as a channel) that transmits and receives signals to and from the connected probe. Conventional general ultrasound diagnostic apparatus uses a switch when the number of channels is less than the number of elements of the transducer. That is, through the switching operation, the ultrasound diagnostic apparatus selectively connects signals received by the elements of a plurality of transducers.

SUMMARY

Therefore, it is an aspect of the disclosure to provide an ultrasound diagnostic apparatus that prevents a faulty channel from receiving an ultrasound signal, and further improves the image quality of an ultrasound image by performing a selective connection using a switch even when the number of channels is greater than the element of the transducer, and a control method thereof.

In accordance with one aspect of the disclosure, an ultrasound diagnostic apparatus includes: a plurality of channels configured to transmit and receive signal with a plurality of transducer elements included in a probe; a beamformer configured to perform beamforming a signal received from a preset number of active channel among the plurality of channels; a switch configured to connect the probe and the plurality of channels; and a controller configured to determine a faulty channel among the plurality of channels, compare whether the number of the plurality of channels is greater than or equal to the number of the plurality of transducer elements and control the switch based on the comparison result when the faulty channel is included in the active channel.

The controller may be configured to select at least one of a standby channel excluding the active channel among the plurality of channels and change the faulty channel to the selected channel.

The controller may be configured to determine a plurality of channels corresponding to at least one transducer element among the plurality of transducer elements and, when a faulty channel is included among the determined plurality of channels, change the faulty channel to at least one channel among the determined plurality of channels.

The controller may be configured to determine a spare channel based on the difference between the number of the plurality of channels and the number of the plurality of transducer elements.

When the faulty channel is included in the active channel, the controller may be configured to change the faulty channel to the spare channel.

The controller may be configured to control the switch so that the plurality of active channels and a standby channel other than the active channel receive signal received by at least one transducer element among the plurality of transducer elements.

The channel may include: a transmitter configured to transmit a pulse signal to the probe; and a receiver configured to receive the signal transmitted from the probe.

The controller may be configured to control the transmitter to transmit the pulse signal to the receiver, compare the normal waveform obtained from the beamformer with a previously stored normal waveform and determine the faulty channel based on the comparison result.

The ultrasound diagnostic apparatus may further include: a signal generator configured to generate a pulse wave signal, the controller may be configured to control the signal generator to transmit the pulse wave signal to the receiver of the plurality of channels, compare the data obtained from the beamformer with the previously stored normal data and determine the faulty channel based on the comparison result.

In accordance with one aspect of the disclosure, a control method of an ultrasound diagnostic apparatus including a plurality of channels; a switch configured to connect a probe and the plurality of channels; and a beamformer configured to perform beamforming a signal received from a preset number of active channel among the plurality of channels, the method includes: determining a faulty channel among the plurality of channels; comparing whether the number of the plurality of channels is greater than or equal to the number of the plurality of transducer elements of the probe; and controlling the switch based on the comparison result when the faulty channel is included in the active channel.

The controlling may include: selecting at least one of a standby channel excluding the active channel among the plurality of channels; and changing the faulty channel to the selected channel.

The controlling may include: determining a plurality of channels corresponding to at least one transducer element among the plurality of transducer elements; and when a faulty channel is included among the determined plurality of channels, changing the faulty channel to at least one channel among the determined plurality of channels.

The controlling may include: determining a spare channel based on the difference between the number of the plurality of channels and the number of the plurality of transducer elements; and when the faulty channel is included in the active channel, changing the faulty channel to the spare channel.

The controlling may include: controlling the switch so that the plurality of active channels and a standby channel other than the active channel receive signal received by at least one transducer element among the plurality of transducer elements.

The channel may include: a transmitter configured to transmit a pulse signal to the probe; and a receiver configured to receive the signal transmitted from the probe.

The determining the faulty channel may include: transmitting the pulse signal to the receiver by the transmitter; comparing the normal waveform obtained from the beamformer with a previously stored normal waveform; and determining the faulty channel based on the comparison result.

The determining the faulty channel may include: generating a pulse wave signal; transmitting the pulse wave signal to the plurality of channels; comparing the data obtained from the receiver of the plurality of channels by the beamformer with the previously stored normal data; and determining the faulty channel based on the comparison result.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 1 is an external perspective view of an ultrasound diagnostic apparatus according to an embodiment.

FIG. 2 is an external view of a probe including a one-dimensional array transducer element.

FIG. 3 is an external view of a probe including a two-dimensional array transducer element.

FIG. 4 is a control block diagram of the disclosed ultrasound diagnostic apparatus.

FIG. 5 is a view of the operation of the ultrasound diagnostic apparatus according to an embodiment.

FIG. 6 is a view of another operation of the ultrasound diagnostic apparatus according to an embodiment.

FIGS. 7 and 8 are diagrams for illustrating an example in which the ultrasound diagnostic apparatus determines a faulty channel.

FIG. 9 is a view of the operation of the ultrasound diagnostic apparatus according to another embodiment.

FIG. 10 is a flow chart of a control method of an ultrasound diagnostic apparatus according to an embodiment disclosed.

FIG. 11 is a flow chart of a control method of an ultrasound diagnostic apparatus according to another embodiment.

DETAILED DESCRIPTION

Like reference numerals refer to like elements throughout the specification. Not all elements of embodiments of the disclosure will be described, and description of what are commonly known in the art or what overlap each other in the embodiments will be omitted. The terms as used throughout the specification, such as "~part," "~module," "~member," "~block," etc., may be implemented in software and/or hardware, and a plurality of "~parts," "~modules," "~members," or "~blocks" may be implemented in a single element, or a single "~part," "~module," "~member," or "~block" may include a plurality of elements.

It will be understood that when an element is referred to as being "connected" to another element, it can be directly or indirectly connected to the other element, wherein the indirect connection includes "connection" via a wireless communication network.

Also, when a part "includes" or "comprises" an element, unless there is a particular description contrary thereto, the part may further include other elements, not excluding the other elements.

Further, when it is stated that a layer is "on" another layer or substrate, the layer may be directly on another layer or substrate or a third layer may be disposed therebetween.

It will be understood that, although the terms first, second, third, etc., may be used herein to describe various elements, it should not be limited by these terms. These terms are only used to distinguish one element from another element.

As used herein, the singular forms "a," "an" and "the" are intended to include the plural forms as well, unless the context clearly indicates otherwise.

An identification code is used for the convenience of the description but is not intended to illustrate the order of each step. Each of the steps may be implemented in an order different from the illustrated order unless the context clearly indicates otherwise.

Hereinafter, the operation principles and embodiments of the disclosure will be described with reference to the accompanying drawings.

FIG. 1 is an external perspective view of an ultrasound diagnostic apparatus according to an embodiment.

Referring to FIG. 1, the ultrasound diagnostic apparatus 1 may be connected to a probe P that transmits an ultrasound signal to an object, receives an echo ultrasound signal from the object, and converts it into an electrical signal.

The ultrasound diagnostic apparatus 1 may be connected to the probe P through a wired communication network or a wireless communication network. The ultrasound diagnostic apparatus 1 may be a work station with a display 30 and an input device 40. In addition, the ultrasound diagnostic apparatus 1 may exchange various information with an external device through a wired communication network or a wireless communication network.

The input device 40 may receive various control commands, such as an operation for the connected probe P and an operation command of the ultrasound diagnostic apparatus 1 that generates an ultrasound image. The input device 40 may be implemented with various hardware devices such as a keyboard, a foot switch, or a foot pedal method. For example, when the input device 40 is implemented as a keyboard, the keyboard may include at least one of a switch, a key, a joystick, and a trackball. As another example, the keyboard may be implemented in software such as a graphic user interface. In this case, the keyboard may be displayed through the second display 52. A foot switch or foot pedal may be provided under the ultrasound diagnostic apparatus 1, and the user may control the operation of the ultrasound diagnostic apparatus 1 by using the foot pedal.

The display 50 may display an ultrasound image generated by the ultrasound diagnostic apparatus 1 and various graphic user interfaces.

The display 50 according to an example may include a first display 51 and a second display 52.

The ultrasound image displayed on the first display 51 may be a two-dimensional ultrasound image or a three-dimensional ultrasound image, and various ultrasound images may be displayed according to the operation mode of the ultrasound diagnostic apparatus 1. In addition, the first display 51 may display not only menus or guides necessary for ultrasound diagnosis, but also information on the operation state of the probe P.

The second display 52 may provide related information such as a menu for optimizing an ultrasound image or an auxiliary image, or may provide a graphic user interface to a user. When the second display 52 serves as the input device 40, a graphic user interface having the same shape as a button included in the input device 40 may be displayed on the second display 52.

On the other hand, the form of the ultrasound diagnostic apparatus 1 is not necessarily limited to that shown in FIG. 1. For example, the ultrasound diagnostic apparatus 1 may be implemented in the form of a smartphone, as well as a laptop, a desktop, and a tablet PC. In addition, the ultrasound diagnostic apparatus 1 may be implemented in the form of a mobile terminal such as a Personal Digital Assistant (PDA), a watch that can be attached to the user's body, and a wearable terminal in the form of glasses.

The object may be a living body of a human or animal, or an in vivo tissue such as blood vessels, bones, muscles, etc., but is not limited thereto, and may be an object as long as its internal structure can be imaged by the ultrasound diagnostic apparatus (1).

Probe P may include a transducer E that is provided in the housing to irradiate ultrasound to an object, receives echo ultrasound reflected from the object, and converts electrical pulse signal and ultrasound to each other, a male connector C that is physically coupled with a female connector 11 of the ultrasound diagnostic apparatus 1 to transmit and receive signals to the ultrasound diagnostic apparatus 1, and a cable B connecting the ultrasound diagnostic apparatus 1 and the probe P.

The transducer E can generate ultrasound according to the applied AC power. Specifically, the transducer E may receive AC power from a power storage device, for example, a battery, inside the probe P. The vibrator (hereinafter, transducer element) of the transducer E can generate ultrasound by vibrating according to the supplied AC power.

In addition, the transducer E receives a signal reflected by the object, that is, echo ultrasound. The transducer E converts the echo ultrasound into an electrical signal. The echo ultrasound has various frequency bands or energy intensity to generate various ultrasound images according to the diagnosis mode.

The probe P transmits the analog signal or digital signal converted from ultrasound by each element of the transducer E to the ultrasound diagnostic apparatus 1 through the cable B. On the other hand, the disclosed probe P is not necessarily connected to the ultrasound diagnostic apparatus 1 through the cable B. The probe P and the ultrasound diagnostic apparatus 1 may transmit and receive signals through wired or wireless communication.

The ultrasound diagnostic apparatus 1 includes a Probe Select Assembly (PSA) board that receives signals transmitted by the probe P. The PSA board may include a plurality of female connectors 11 so that a plurality of probes P can be connected, and may include a switch (10, see FIG. 4) and a plurality of channels (20, see FIG. 4) provided inside the PSA board. The PSA board transmits the received signal to the beamformer 30 (see FIG. 4). A detailed description of the ultrasound diagnostic apparatus 1 will be described later through other drawings.

FIG. 2 is an external view of a probe including a one-dimensional array transducer element. FIG. 3 is an external view of a probe including a two-dimensional array transducer element.

As described above in FIG. 1, the probe P converts the pulse signal received from the main body into an ultrasound signal, transmits the ultrasound signal to a specific area inside the object, and receives the echo ultrasound signal reflected from a specific area inside the object, converts it back into a pulse signal, and transmits it to the ultrasound diagnostic apparatus 1.

The probe P may include a transducer element that converts an electrical pulse signal and an ultrasound signal to each other in order to transmit an ultrasound signal into the object. The transducer array is composed of a single or a plurality of transducer elements.

The transducer array may be a one-dimensional array or a two-dimensional array. In an embodiment, the transducer E may include a one-dimensional transducer array as shown in FIG. 2.

Each of the transducer elements constituting the one-dimensional transducer array may convert the ultrasonic signal into an electrical signal and vice versa. For this, the transducer element may be a magnetostrictive ultrasonic transducer using the magnetostrictive effect of a magnetic material, a piezoelectric ultrasonic transducer or a piezoelectric Micromachined Ultrasonic Transducer (pMUT) using the piezoelectric effect of a piezoelectric material, or a capacitive Micromachined Ultrasonic Transducer (cMUT) that transmits and receives ultrasonic waves using vibration of several hundreds or thousands of micromachined thin films.

Meanwhile, the one-dimensional transducer array may be linearly aligned or may be convexly aligned as shown in FIG. 2. In both cases, the ultrasonic probe P may operate according to the same operation principle, however, when the ultrasonic probe P includes the convex transducer E in a convex shape, the ultrasonic waves irradiated from the transducer E may be in the shape of a fan, and accordingly, the ultrasonic image may also be created in the shape of a fan.

As another example, the transducer E may include a two-dimensional transducer array as shown in FIG. 3. In the case of including a 2D transducer array, the interior of the object can be imaged in 3D. In addition, even if the transducer array of the probe P is arranged in one dimension, the probe P may mechanically move the 1D transducer array and transmit an echo ultrasound signal capable of generating a 3D ultrasound image to the ultrasound diagnostic apparatus 1 by acquiring volume information inside the object.

Each transducer element constituting the 2D transducer array may be the same as the transducer element constituting the 1D transducer array.

Meanwhile, the 2D transducer array may include a larger number of transducer elements than the 1D transducer array. The ultrasound diagnostic apparatus 1 includes a plurality of channels 20 to receive signals transmitted by a large number of transducer elements.

Conventionally, when the number of channels is less than the transducer element of the connected probe P, the conventional general ultrasound diagnostic apparatus processes the received signal by using the switch 10. However, the disclosed ultrasound diagnostic apparatus 1 performs signal processing through the switch 10 even when the number of channels is greater than the transducer element of the probe P to which it is connected.

FIG. 4 is a control block diagram of the disclosed ultrasound diagnostic apparatus.

Referring to FIG. 4, the ultrasound diagnostic apparatus 1 includes a switch 10 connecting a channel with a transducer element, a plurality of channels 20 for transmitting and receiving signals with a plurality of transducer elements included in the probe, a beamformer 30 for beamforming a signal received from a preset number of active channels among a plurality of channels 20, a signal processor 60 that generates an ultrasound image through the signal delayed by the beamformer 30 and performs image processing, an input device 40 that receives input information from a user, a display 50 displaying ultrasound image and various user interfaces, and a controller 100 for controlling the above configuration and the overall configuration of the ultrasound diagnostic apparatus 1.

The switch 10 may be provided on the PSA board, and connect a plurality of channels 20 and a transducer element, respectively. The switch 10 may be provided as a relay that enables mechanical detachment, or may be provided as a semiconductor device that performs electrical switching.

The channel 20 may include a transmitter 21 that transmits a pulse signal to the probe P, and a receiver 22 that receives electrical signals converted from echo ultrasound by probe P. The ultrasound diagnostic apparatus 1 may include a plurality of channels 20 each including a transmitter 21 and a receiver 22.

Specifically, the transmitter 21 generates a pulse signal that controls the probe P, and transmits the pulse signal to the probe P through the cable B. Also, the transmitter 21 may transmit a pulse signal to the receiver 22 to determine a faulty channel.

The receiver 22 may include a Low Noise Amplifier (LNA) that amplifies an electrical signal transmitted from the probe P, and an Analog to Digital Converter (ADC) that converts an analog signal transmitted from the probe P into a digital signal.

The receiver 22 transmits the signal received from the probe P to the beamformer 30. In addition, the receiver 22 may transmit the pulse wave signal generated by the signal generator 70 to the beamformer 30 in order to determine a faulty channel.

The beamformer 30 is a device that performs an appropriate delay time for the irradiated ultrasound or the received echo ultrasound to focus the ultrasound generated from the transducer element of the probe P at a target point of the object at the same time, or to overcome the difference in time for the echo ultrasound reflected from the target point of the object to reach the transducer element.

In order to improve the quality of the ultrasound image, the signal processor 60 filters noise components from the digital receiving focused beam, performs an envelope detection process that detects the intensity of the received signal based on the filtered received focused beam, and generates ultrasound image data.

The signal processor 60 performs scan conversion for converting a scan line of the ultrasound image data so that the ultrasound image data can be displayed on the display 50. The signal processor 60 also performs image processing such as B mode image processing and Doppler image processing on digital ultrasound image data based on scan-converted digital ultrasound image data in order to display the ultrasound image of the type desired by the user.

The signal processor 60 processes the ultrasound image data in RGB and transmits it to the display 50 so that the image-processed digital ultrasound image data can be displayed as an ultrasound image.

The display 50 may display the generated ultrasound image and various information processed by the ultrasound diagnostic apparatus 1. The ultrasound diagnostic apparatus 1 may include one or a plurality of display 51 and 52 depending on the implementation type. Also, the display 50 may be implemented as a touch screen in combination with a touch panel.

The input device 40 receives a control command from a user. For example, the input device 40 may receive information on the number of transducer elements of the connected probe P. The input device 40 transmits the received information to the controller 100. The controller 100 may compare the number of channels 20 based on the received information and control the switch 10.

The controller 100 is a processor that controls the overall ultrasound diagnostic apparatus 1. For example, after receiving the echo ultrasound signal reflected on the object from the probe P, the controller 100 may display the ultrasound image generated through the beamformer 30 and the signal processor 60 through the display.

In the disclosed embodiment, the controller 100 compares whether the number of channels 20 is greater than or equal to the number of transducer elements. Among the plurality of channels 20, there may be a faulty channel. When the number of the plurality of channels 20 is greater than the number of transducer elements, the controller 100 secures a connection state with the probe P by connecting the remaining channels with the transducer element instead of the faulty channel. A detailed description of the control method of the controller 100 will be described later through other drawings below.

The controller 100 may further include a ROM in which a control program for controlling the ultrasound diagnostic apparatus 1 is stored and a RAM used as a storage area corresponding to various operations performed in the ultrasound diagnostic apparatus 1. In addition, the controller 100 may be implemented as a graphic processing board including the above-described processor, RAM, or ROM on a circuit board, and the processor, RAM, and ROM may be interconnected through an internal bus.

The signal generator 70 generates a pulse wave signal in order for the controller 100 to determine a faulty channel. The pulse wave signal generated by the signal generator 70 is transmitted to all channels 20 provided. The controller 100 may compare the waveform transmitted from the receiver 22 of all channels 20 through the beamformer 30 with a previously stored normal waveform, and determine a faulty channel based on the comparison result. A detailed description of determining the faulty channel will be described later through other drawings.

Meanwhile, the disclosed ultrasound diagnostic apparatus 1 may further include other components not described in FIG. 4, and the mutual positions of the components may be changed in response to the performance or structure of the system.

FIG. 5 is a view of the operation of the ultrasound diagnostic apparatus according to an embodiment.

Referring to FIG. 5, the ultrasound diagnostic apparatus 1 may be connected to a probe P including 192 transducer elements (#E1 to #E192). The disclosed ultrasound diagnostic apparatus 1 may include more than or equal to 192 channels 20.

The ultrasound diagnostic apparatus 1 may set an active channel (active aperture) for every 66 channels among 192 channels. That is, the ultrasound diagnostic apparatus 1 does not receive echo ultrasound through 192 transducer elements at once, but divides and receives echo ultrasound from a preset number of active channels. For example, the ultrasound diagnostic apparatus 1 receives echo ultrasound from a first transducer element (E #1) to a 66th transducer element (E #66). And the ultrasound diagnostic apparatus 1 receives echo ultrasound from the second transducer element (E #2) to the 67th transducer element (E #67). And the ultrasound diagnostic apparatus 1 receives echo ultrasound from the third transducer element (E #3) to the 68th transducer element (E #68). In this way, the ultrasound diagnostic apparatus 1 receives an echo ultrasound while sequentially changing an active channel among a plurality of channels 20. Among the plurality of channels 20, the remaining channels other than the active channel are referred to as standby channels (Idle Aperture).

While sequentially receiving echo ultrasound, the ultrasound diagnostic apparatus 1 may receive echo ultrasound using an active channel corresponding to the 64th transducer element (E #64) to the 129th transducer element (E #129). However, the 88th channel (CH #88) receiving echo ultrasound from the 88th transducer element (E #88) may be a faulty channel. The ultrasound diagnostic apparatus 1 does not receive echo ultrasound from the 88th channel (CH #88), which is a faulty channel, but connects at least one of the standby channels, for example, the first channel (CH #1) to the 88th transducer element (E #88). That is, the ultrasound diagnostic apparatus 1 connects the first channel CH #1 and the 88th transducer element E #88 through the switch 10. Through this, the ultrasound diagnostic apparatus 1 can improve the quality of the ultrasound image.

FIG. 6 is a view of another operation of the ultrasound diagnostic apparatus according to an embodiment.

Referring to FIG. 6, The ultrasound diagnostic apparatus 1 may include a greater number of transducer elements than the connected probe P, that is, 192 or more channels 20. However, unlike FIG. 5, the ultrasound diagnostic apparatus 1 may include a spare channel 23 for a faulty channel.

Specifically, when the ultrasound diagnostic apparatus 1 determines the faulty channel, the ultrasound diagnostic apparatus 1 may disconnect the faulty channel and the corresponding transducer element. The ultrasound diagnostic apparatus 1 may prevent channel loss by connecting the transducer element and the spare channel 23.

The ultrasound diagnostic apparatus 1 may set the spare channel 23 based on a difference between the number of provided channels 20 and the number of transducer elements of the connected probe P. In addition, the ultrasound diagnostic apparatus 1 may correspond each spare channel 23 with a plurality of transducer elements, and prepare for a faulty channel.

As shown in FIG. 6, the ultrasound diagnostic apparatus 1 may set a first spare channel 23-1 as a spare channel of a first transducer element (E #1), a second transducer element (E #2), a 64th transducer element (E #64) and a 65th transducer element (E #65). If the 64th channel (CH #64) is determined to be a faulty channel, the ultrasound diagnostic apparatus 1 may connect the first spare channel 23-1 set as the spare channel of the 64th channel (CH #64) and the 64th transducer element (#64).

Meanwhile, the number of channels and transducer elements described in FIGS. 5 and 6 is only an example. That is, the disclosed ultrasound diagnostic apparatus 1 compares the number of transducer elements of the connected probe P with the number of channels 20, and when the number of channels 20 is greater than or equal to the number of transducer elements, connects a faulty channel to a standby channel or a spare channel.

FIGS. 7 and 8 are diagrams for illustrating an example in which the ultrasound diagnostic apparatus determines a faulty channel.

Referring first to FIG. 7, the ultrasound diagnostic apparatus 1 transmits a pulse signal to each channel 20 in order to determine whether the transmitter 21 has failed. Specifically, the controller 100 generates a pulse signal allocated to the first channel CH #1 and transmits the pulse signal to the first channel CH #1. The transmitter 21 of the first channel CH #1 transmits the received pulse signal to the receiver 22 of the first channel CH #1. The beamformer 30 acquires data received from the receiver 22 of the first channel CH #1, that is, a pulse shape. The controller 100 compares the pulse shape obtained from the beamformer 30 with a previously stored normal waveform, and determines whether or not the first channel CH #1 has a failure based on the comparison result. If the acquired pulse shape does not match the normal waveform, the controller 100 may determine the transmitter 21 of the first channel CH #1 as a failure and determine the first channel CH #1 as a faulty channel.

Meanwhile, after determining whether the first channel (CH #1) has failed, the ultrasound diagnostic apparatus 1 repeats the above-described sequence for the second channel CH #2 and the third channel CH #3, and determines whether the channel has failed.

Referring to FIG. 8, the controller 100 generates a pulse wave signal through the signal generator 70. The controller 100 transmits the generated pulse wave signal to all of the receivers 22 of the plurality of channels 20. For example, the controller 100 simultaneously transmits a pulse wave signal to the receiver 22 of the first channel (CH #1), the second channel (CH #2) and the third channel (CH #3) as shown in FIG. 8. The beamformer 30 acquires data transmitted from the receivers 22 of all channels 20. The controller 100 compares the acquired data with previously stored normal data. The controller 100 determines whether there is a failure based on the comparison result.

Meanwhile, the above-described embodiment in FIGS. 7 and 8 is only an example for determining the faulty channel, and the faulty channel may be determined through another method.

FIG. 9 is a view of the operation of the ultrasound diagnostic apparatus according to another embodiment.

Referring to FIG. 9, the ultrasound diagnostic apparatus 1 compares the number of transducer elements of the connected probe P with the number of channels 20. If the number of channels 20 is greater than or equal to the number of transducer elements, the ultrasound diagnostic apparatus 1 may improve signal to noise ratio (SNR) through a standby channel other than an active channel.

Specifically, the ultrasound diagnostic apparatus 1 can receive echo ultrasound from 66 active channels. The ultrasound diagnostic apparatus 1 can connect channels other than the 66th channel (CH #66) to the 129th channel (CH #129), that is, the first channel (CH #1), the second channel (CH #2), the 191th channel (CH #191) and the 192nd channel (CH #192) to the 64th transducer element (E #64) to the 129th transducer element (E #129). That is, the ultrasound diagnostic apparatus 1 may improve SNR by corresponding to one transducer element with one active channel and at least one standby channel, and controlling at least two or more channels to receive echo ultrasound.

FIG. 10 is a flow chart of a control method of an ultrasound diagnostic apparatus according to an embodiment disclosed.

Referring to FIG. 10, the ultrasound diagnostic apparatus 1 determines a faulty channel among a plurality of channels 20 (200).

Methods of determining a faulty channel can be varied.

For example, the ultrasound diagnostic apparatus 1 transmits a pulse signal to the transmitter 21 of the channel 20, and controls the transmitter 21 to transmit the pulse signal to the receiver 22. The ultrasound diagnostic apparatus 1 may determine whether the transmitter 21 has failed by comparing the data acquired by the beamformer 30 from the receiver 22 with a previously stored normal waveform. The ultrasound diagnostic apparatus 1 can determine a faulty channel by repeating the above-described operation for each channel.

As another example, the ultrasound diagnostic apparatus 1 generates a pulse waveform through the signal generator 70 and transmits the pulse wave signal to the receiver 22 of all channels 20. The ultrasound diagnostic apparatus 1 may determine whether the receiver 22 has failed by comparing the data acquired by the beamformer 30 from the receiver 22 with a previously stored normal waveform.

The ultrasound diagnostic apparatus 1 is connected to the probe P (210), and compares the number of transducer elements and the number of channels 20 (220).

If the number of transducer elements is greater than or equal to the number of the plurality of channels 20, the ultrasound diagnostic apparatus 1 controls the switch 10 like a conventional ultrasound diagnostic apparatus.

If the number of transducer elements is less than the number of the plurality of channels 20, the ultrasound diagnostic apparatus 1 changes the faulty channel to a spare channel or a standby channel by controlling the switch 10 as described above (230).

For example, the ultrasound diagnostic apparatus 1 may select at least one of a standby channel excluding an active channel among a plurality of channels, and change the determined faulty channel to the selected channel.

As another example, the ultrasound diagnostic apparatus 1 calculates the difference between the number of the plurality of channels 20 and the number of the plurality of transducer elements. The ultrasound diagnostic apparatus 1 selects a spare channel based on the calculated difference. If there is a faulty channel determined among active channels, the ultrasound diagnostic apparatus 1 changes the faulty channel to a spare channel.

FIG. 11 is a flow chart of a control method of an ultrasound diagnostic apparatus according to another embodiment.

Referring to FIG. 11, the ultrasound diagnostic apparatus 1 compares the number of channels 20 with the number of transducer elements (300).

For example, the ultrasound diagnostic apparatus 1 may confirm the number of transducer elements of the connected probe P based on a control command input from a user. The ultrasound diagnostic apparatus 1 compares the number of transducer elements received from the input device 40 with the number of built-in channels 20.

The ultrasound diagnostic apparatus 1 determines whether a faulty channel is included in the active channel (310).

If there is no faulty channel, the ultrasound diagnostic apparatus 1 connects channels other than the active channel, for example a spare channel or a standby channel, in duplicate. For example, the ultrasound diagnostic apparatus 1 may connect a one active channel and one standby channel to a one transducer element in duplicate. Through this, the disclosed ultrasound diagnostic apparatus 1 can improve SNR.

If a faulty channel is included, the ultrasound diagnostic apparatus 1 disconnects the faulty channel of the active channel and the transducer element, and controls the switch 10 so that the spare channel or the standby channel and the transducer element are connected.

The ultrasound diagnostic apparatus and control method thereof according to the disclosed aspect can prevent a faulty channel from receiving an ultrasound signal, and further improve the image quality of an ultrasound image by performing a selective connection using a switch even when the number of channels is greater than the element of the transducer, and a control method thereof.

What is claimed is:

1. An ultrasound diagnostic apparatus comprising:
   a plurality of active channels configured to transmit and receive signal with a plurality of transducer elements comprised in a probe, each of the plurality of active channels being connected to each of the plurality of transducer elements;
   a plurality of spare channels each able to be connected to at least two transducer elements among the plurality of transducers;
   a beamformer configured to perform beamforming a signal received from the plurality of active channels;
   a switch configured to connect the probe with the plurality of active channels and the plurality of spare channels; and
   a controller configured to determine a faulty channel among the plurality of active channels, and when the faulty channel is comprised in the plurality of active channels, control the switch such that the faulty channel is replaced by a spare channel able to be connected to a transducer element corresponding to the faulty channel among the plurality of spare channels.

2. The ultrasound diagnostic apparatus according to claim 1,
   wherein, when the faulty channel is comprised in the active channel, the controller is configured to control the switch to disconnect the faulty channel with the transducer element corresponding to the faulty channel, and connect the transducer element corresponding to the faulty channel with the spare channel.

3. The ultrasound diagnostic apparatus according to claim 1, further comprises a plurality of standby channels,
   wherein the controller is configured to control the switch so that at least one of the plurality of active channels and at least one of the plurality of standby channels receive signal received by at least one transducer element among the plurality of transducer elements.

4. The ultrasound diagnostic apparatus according to claim 1,
   wherein each of the plurality of active channels and the plurality of spare channels comprises:
   a transmitter configured to transmit a pulse signal to the probe; and
   a receiver configured to receive the signal transmitted from the probe.

5. The ultrasound diagnostic apparatus according to claim 4,
   wherein the controller is configured to control the transmitter to transmit the pulse signal to the receiver, compare a waveform obtained from the beamformer with a previously stored waveform and determine the faulty channel based on the comparison result.

6. The ultrasound diagnostic apparatus according to claim 4, further comprising:
   a signal generator configured to generate a pulse wave signal,
   wherein the controller is configured to control the signal generator to transmit the pulse wave signal to the receiver of the plurality of active channels, compare data obtained from the beamformer with previously stored data and determine the faulty channel based on the comparison result.

7. A control method of an ultrasound diagnostic apparatus comprising a plurality of active channels configured to transmit and receive signal with a plurality of transducer elements comprised in a probe, each of the plurality of active channels being connected to each of the plurality of transducer elements; a plurality of spare channels each able to be connected to at least two transducer elements among the plurality of transducers; a switch configured to connect the probe with the plurality of active channels and the plurality of spare channels; and a beamformer configured to perform beamforming a signal received from the plurality of active channels, the method comprises:

determining a faulty channel among the plurality of active channels; and when the faulty channel is comprised in the plurality of active channels, controlling the switch such that the faulty channel is replaced by a spare channel able to be connected to a transducer element corresponding to the faulty channel among the plurality of spare channels.

8. The control method according to claim 7, wherein the ultrasound diagnostic apparatus further comprises a plurality of standby channels, wherein the controlling comprises:

controlling the switch so that at least one of the plurality of active channels and at least one of the plurality of standby channels receive signal received by at least one transducer element among the plurality of transducer elements.

9. The control method according to claim 7, wherein each of the plurality of active channels and the plurality of spare channels comprises:

a transmitter configured to transmit a pulse signal to the probe; and a receiver configured to receive the signal transmitted from the probe.

10. The control method according to claim 9, wherein the determining the faulty channel comprises:

transmitting the pulse signal to the receiver by the transmitter;

comparing a waveform obtained from the beamformer with a previously stored waveform; and determining the faulty channel based on the comparison result.

11. The control method according to claim 9, wherein the determining the faulty channel comprises:

generating a pulse wave signal;

transmitting the pulse wave signal to the plurality of active channels;

comparing data obtained from the receiver of the plurality of active channels by the beamformer with previously stored data; and determining the faulty channel based on the comparison result.

* * * * *